United States Patent
Mendyk

(10) Patent No.: US 10,557,580 B2
(45) Date of Patent: Feb. 11, 2020

(54) SECURE FLUID CONNECTION

(71) Applicant: SARTORIUS STEDIM FMT SAS, Aubagne (FR)

(72) Inventor: Nicolas Mendyk, Peypin (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 1135 days.

(21) Appl. No.: 14/784,609

(22) PCT Filed: Apr. 10, 2014

(86) PCT No.: PCT/FR2014/050865
§ 371 (c)(1),
(2) Date: Oct. 15, 2015

(87) PCT Pub. No.: WO2014/170584
PCT Pub. Date: Oct. 23, 2014

(65) Prior Publication Data
US 2016/0076679 A1   Mar. 17, 2016

(30) Foreign Application Priority Data

Apr. 15, 2013   (FR) ...................................... 13 53382

(51) Int. Cl.
*F16L 37/098* (2006.01)
*A61M 39/10* (2006.01)
(Continued)

(52) U.S. Cl.
CPC ...... *F16L 37/0982* (2013.01); *A61M 39/1011* (2013.01); *F16L 37/0841* (2013.01); (Continued)

(58) Field of Classification Search
CPC ..... F16L 21/08; F16L 37/0841; F16L 37/098; F16L 37/0985; F16L 2201/10;
(Continued)

(56) References Cited

U.S. PATENT DOCUMENTS

| | | | |
|---|---|---|---|
| 5,401,063 A | * | 3/1995 | Plosz ................. F16L 37/0985 285/81 |
| 5,649,724 A | | 7/1997 | Wiethorn |

(Continued)

FOREIGN PATENT DOCUMENTS

| | | |
|---|---|---|
| DE | 37 10 853 A1 | 10/1988 |
| EP | 0 462 971 B1 | 1/1992 |

(Continued)

OTHER PUBLICATIONS

International Search Report, dated Aug. 1, 2014, from corresponding PCT application.

*Primary Examiner* — Zachary T Dragicevich
(74) *Attorney, Agent, or Firm* — Young & Thompson

(57) ABSTRACT

A fluid connection device (10) for connecting two fluid conduits (11, 12), includes a female plug (1), a male plug (2), intended to be inserted into the female plug into a final coupling position, a movable primary locking device (3), having a locked position (30) in which it prevents the male and female plugs from being released from the final coupling position, and a movable secondary latch (4) having an active position (40) designed to prevent the primary locking device (3) from being moved out of the locked position of same, whereby the fluid connection device can establish a permanent connection of the first and second conduits.

13 Claims, 5 Drawing Sheets

(51) Int. Cl.
*F16L 37/084* (2006.01)
*F16L 21/08* (2006.01)

(52) U.S. Cl.
CPC .... *F16L 37/098* (2013.01); *A61M 2039/1027* (2013.01); *F16L 21/08* (2013.01); *F16L 2201/10* (2013.01); *F16L 2201/20* (2013.01)

(58) Field of Classification Search
CPC ............ F16L 2201/20; A61M 39/1011; A61M 2039/1027
USPC .................................... 285/81, 93, 322, 319
See application file for complete search history.

(56) References Cited

U.S. PATENT DOCUMENTS

| | | | |
|---|---|---|---|
| 2006/0208743 | A1 | 9/2006 | Ishida et al. |
| 2008/0252071 | A1 | 10/2008 | Lechner et al. |
| 2009/0035055 | A1* | 2/2009 | Rosch ................ F16L 37/0982 |
| 2010/0019487 | A1 | 1/2010 | deCler et al. |
| 2010/0284732 | A1 | 11/2010 | Nakamura |
| 2012/0119485 | A1* | 5/2012 | Cichorek ............ F16L 37/0982 |
| | | | 285/81 |
| 2012/0319401 | A1* | 12/2012 | Wang ................ F16L 37/0985 |

FOREIGN PATENT DOCUMENTS

| | | |
|---|---|---|
| EP | 2224158 | 9/2010 |
| FR | 1487324 | 7/1967 |

\* cited by examiner

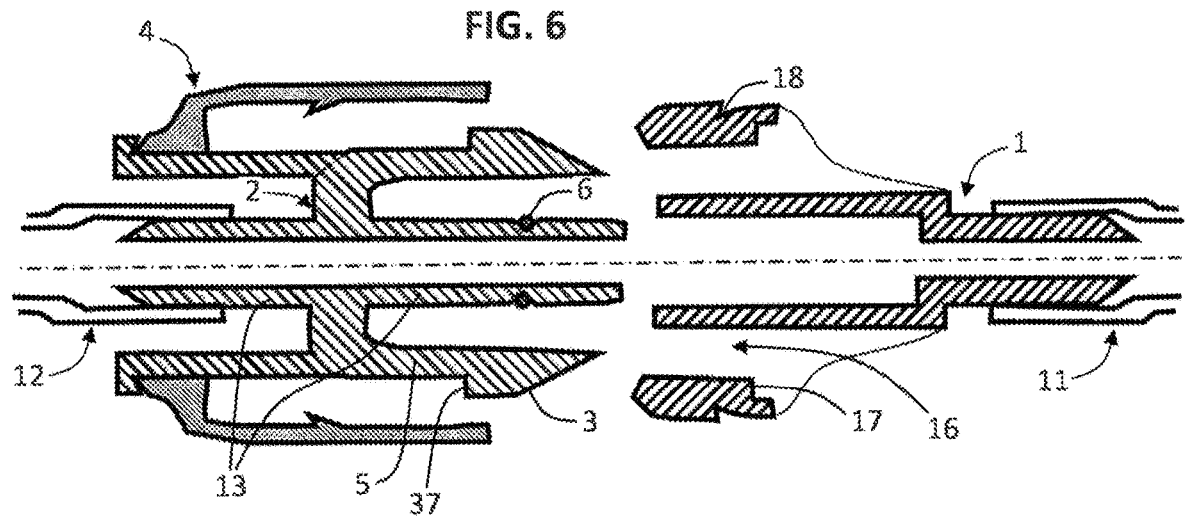
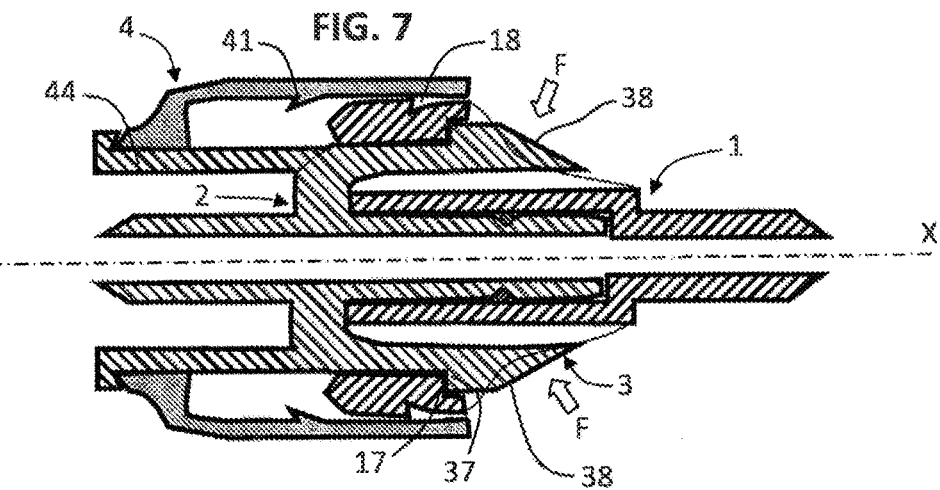
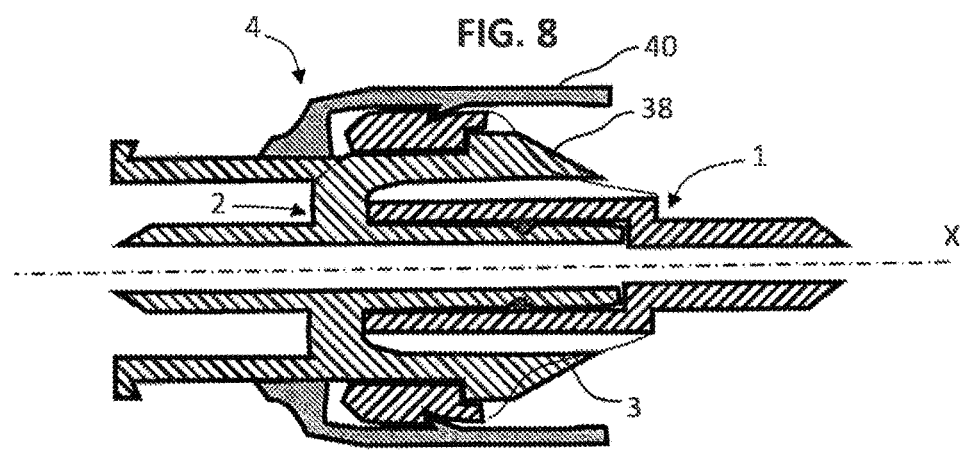

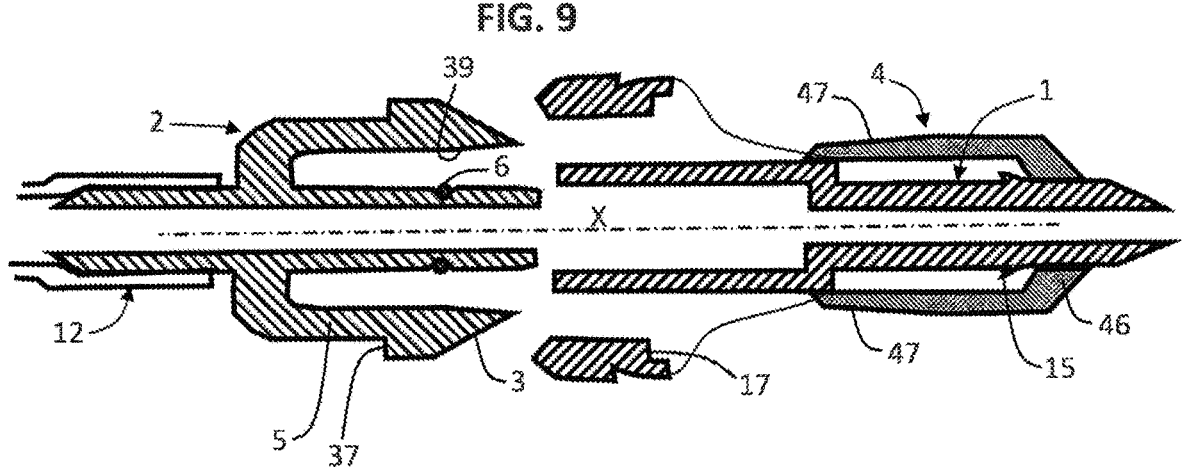
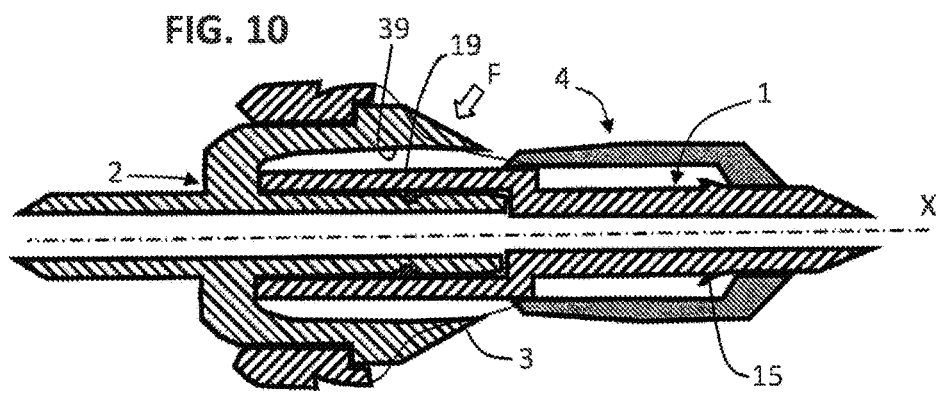
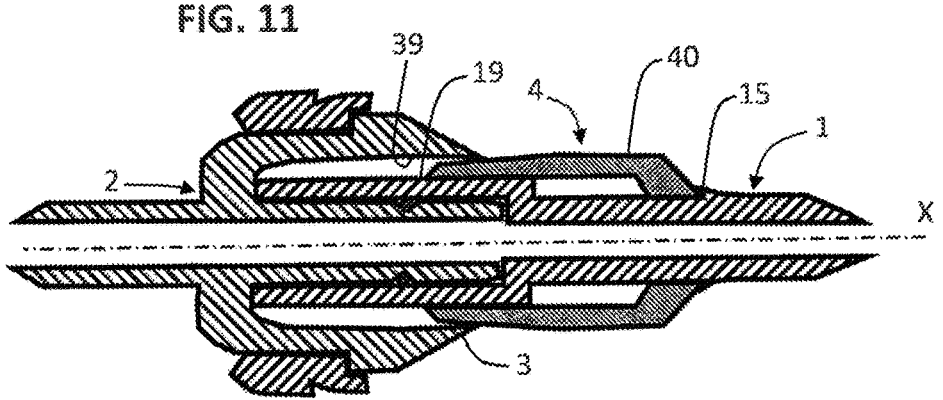

SECURE FLUID CONNECTION

The present invention relates to fluid connection devices, in particular for connecting together two fluid conduits.

More particularly, the invention relates to a fluid connection device for interconnecting two fluid conduits, also called a connecting or coupling device. The fluid may be liquid, gaseous, or pasty, and the conduit may be a pipe or a conduit internal to a device.

BACKROUND OF THE INVENTION

It is known, in particular from document EP0462971, to use a fluid connection device to connect a first fluid conduit to a second fluid conduit, comprising:
- a female plug, made of plastic and joined to the first fluid conduit,
- a male plug, made of plastic, joined to the second fluid conduit, and intended for insertion into the female plug into a final coupling position, and
- a movable primary locking device, having a locked position in which it prevents the male and female plugs from being released from the final coupling position.

However, in this document EP0462971, no means are provided for securing the connection to prevent unwanted detachment.

It has been found that in some cases it may be advantageous to secure the connection when in the actual connection position, to prevent subsequent undesired detachment.

SUMMARY OF THE INVENTION

To this end, the invention proposes a fluid connection device of the type mentioned above, characterized in that it comprises a movable secondary lock having an active position adapted to prevent the primary locking device from being moved out of its locked position, the secondary lock being configured to be irreversibly clipped into place in its active position, whereby the fluid connection device can establish a permanent connection (i.e. a definitive connection) of the first and second conduits.

With these arrangements, the fluid connection device can first be used reversibly by engaging the primary locking device, and then said connection can be made impossible to disassemble by placing the secondary locking device in its active position, in an irreversible manner; when the secondary lock reaches its active position, this position connection can no longer be exited by any user operation, which makes the connection permanent (i.e. definitive). In a medical, spatial, or other environment, the connection can thus be secured, which is advantageous for ensuring that no unwanted disconnection can take place, and which is advantageous for ensuring that the chain of sterility remains intact and that aseptic conditions are continuously maintained.

In embodiments of the method according to the invention, one or more of the following arrangements may possibly be used:
- the secondary locking device may prevent any operative access to the primary locking device; this represents a relatively simple solution for making the connection impossible to disassemble;
- the secondary locking device may prevent the primary locking device from moving out of its locked position; this represents a particularly robust solution for ensuring that disassembly is impossible;
- the primary locking device is biased toward its locked position by elastic biasing means; such that the default position is the locked position;
- the secondary locking device can only be brought to its active position if the primary locking device is in its locked position; whereby proper coupling is ensured;
- the secondary locking device can only be brought into active position if the primary locking device is in its locked position and simultaneously the female plug and male plug are in the final coupling position; whereby proper coupling is further ensured and visual verification of the connection is further improved;
- the secondary locking device is arranged on one of the male or female plugs, and is configured to be moved from an inactive position to an active position in order to lock the connection permanently; so that permanent locking of the connection only occurs after a deliberate action of moving the secondary lock;
- the primary locking device forms a part distinct from the female plug; it is thus possible to choose a different material, in particular according to biocompatibility constraints and elasticity requirements;
- the secondary lock is part of the female plug;
- the secondary lock is part of the male plug;
- the primary locking device is arranged on the female plug; whereby the male plug is particularly simple to manufacture;
- the primary locking device is formed by two diametrically opposite clips; which represents a solution of limited radial footprint.

In another aspect, which can be independent of the irreversibility of the clipping the secondary lock into place, said secondary lock may be provided as a separate part, supplied and moved separately from the male and female plugs, and clipped into place at the time of the permanent locking. In this manner it is easy to recognize a secured connection by the presence of the secondary lock, whether or not it is reversible.

Besides, the invention also relates to a female plug for fluid connection, comprising an embedded primary locking device and configured to receive a secondary lock having an active position adapted to prevent manipulation of the primary locking device from its locked position, the active position being irreversible.

BRIEF DESCRIPTION OF THE DRAWING

Other features and advantages of the invention will become apparent from the following description of three of its embodiments, given by way of non-limiting examples with reference to the accompanying drawings.

In the drawings:

FIG. 6 is a schematic view of a connection device according to a second embodiment of the invention, represented in the uncoupled state, FIG. 7 shows the connection device of FIG. 6, represented in the coupled state, FIG. 8 shows the connection device of FIG. 6, represented in the coupled and secured state, FIG. 9 is a schematic view of a connection device according to a third embodiment of the invention, represented in the uncoupled state, FIG. 10 shows the connection device of FIG. 9, represented in the coupled state, FIG. 11 shows the connection device of FIG. 9, represented in the coupled and secured state.

DETAILED DESCRIPTION OF THE PREFERRED EMBODIMENTS

In the various figures, the same references designate identical or similar elements.

Figure 1:
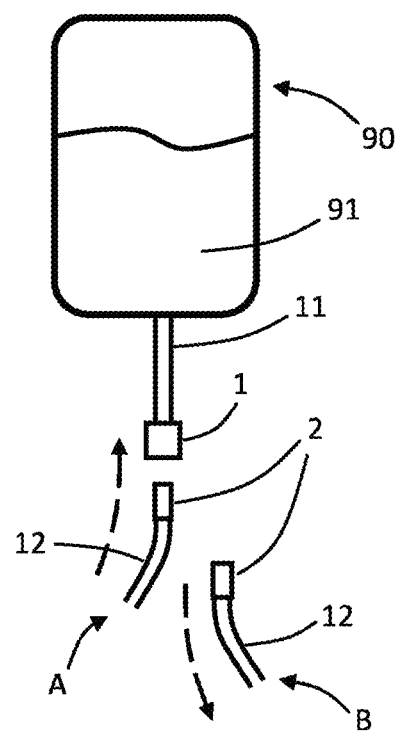
FIG. 1 shows an example system in which a connection device according to the invention is used.

As represented in FIG. 1, a container pouch 90 is provided for containing biopharmaceutical fluid 91; this usage may require aseptic precautions. In the context of the invention, the term "biopharmaceutical fluid" is understood to mean a fluid derived from biotechnology—culture media, cell cultures, buffer solutions, artificial nutrition liquids—or a pharmaceutical fluid or more generally a fluid intended for use in the medical field. A first fluid conduit 11 places the internal volume of the container pouch 90 in communication with a connection plug 1 (or connector). In the example shown, this plug is a female plug (female connector) which is adapted to receive the complementary form of a male plug 2 to which a second fluid conduit 12 is connected.

In one example usage, to begin with one connects a first device 'A' having a second fluid conduit 12 and a male connector 2, for example in order to fill the container pouch 90. Adequate connection between the male and female plugs must be ensured, but it must be possible to disconnect the connection (also referred to as uncoupling the coupling) once the filling operation is completed.

The container pouch can then be used at a different location and in a different context if such is appropriate. In particular, said container pouch 90 can be used to supply a fluid distribution system or a product dispensing device, denoted 'B' in FIG. 1, in which case the container pouch 90 will empty into a user flow system. The application context may require that it be impossible to separate the flexible pouch and at least a portion of the user flow system, particularly in the case of disposable parts which are discarded after use, but also in the case where the chain of sterility must be preserved. The connection will therefore be placed in a configuration where it is impossible to disconnect the connector by any manipulation, the connection then considered as being permanent.

Figure 2:
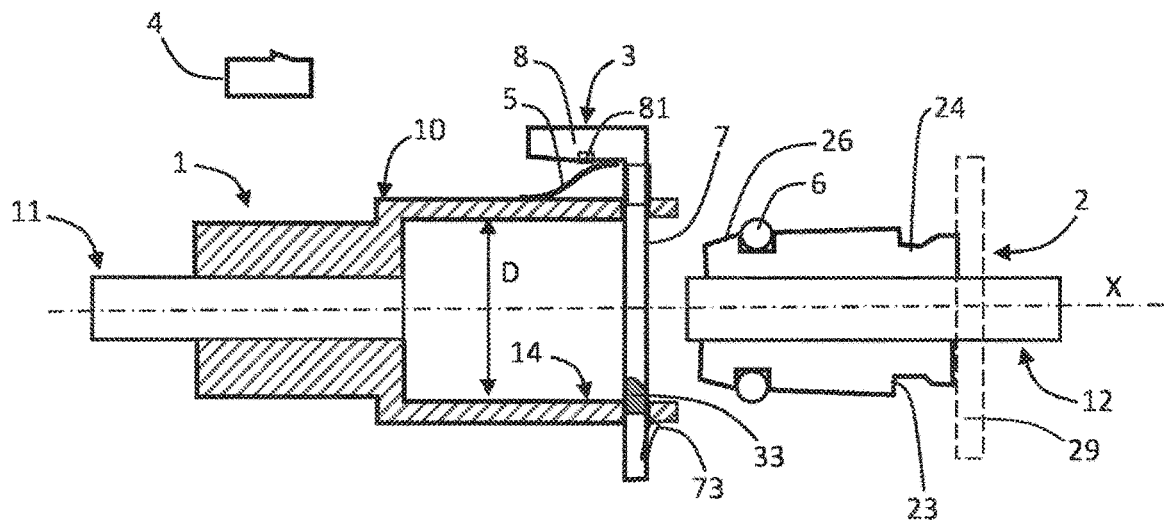
FIG. 2 is a schematic view of a connection device according to a first embodiment of the invention, represented in the uncoupled state.
Figure 3:
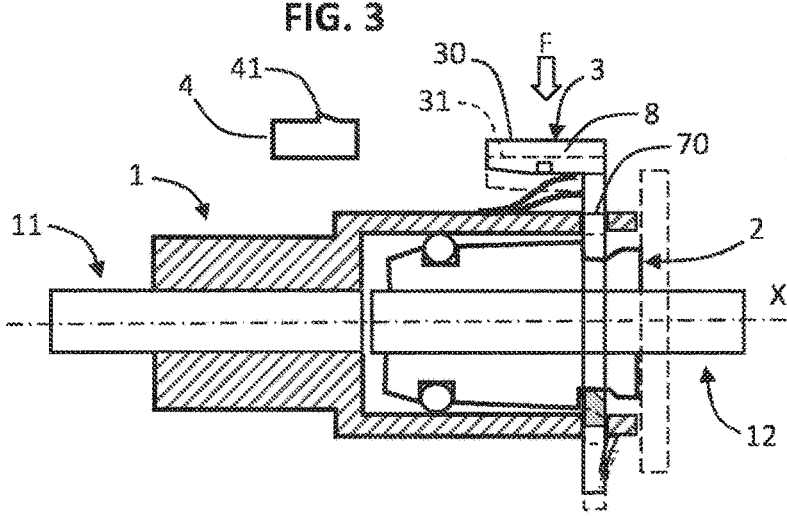
FIGS. 3 and 3A show the connection device of FIG. 2, represented in the coupled state.
Figure 3A:
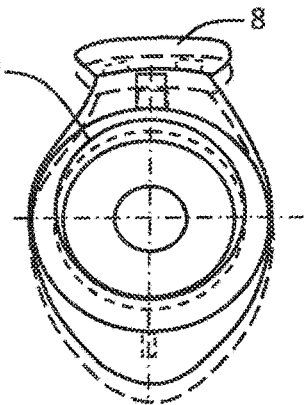

FIGS. 2, 3, 3A, 4 and 4A illustrate a first embodiment of the fluid connection, comprising a female plug 1, and a male plug 2 intended to be inserted into the female plug, into the final coupling position represented in FIG. 3, in a coupling/decoupling movement parallel to the axial direction X.

Figure 4:
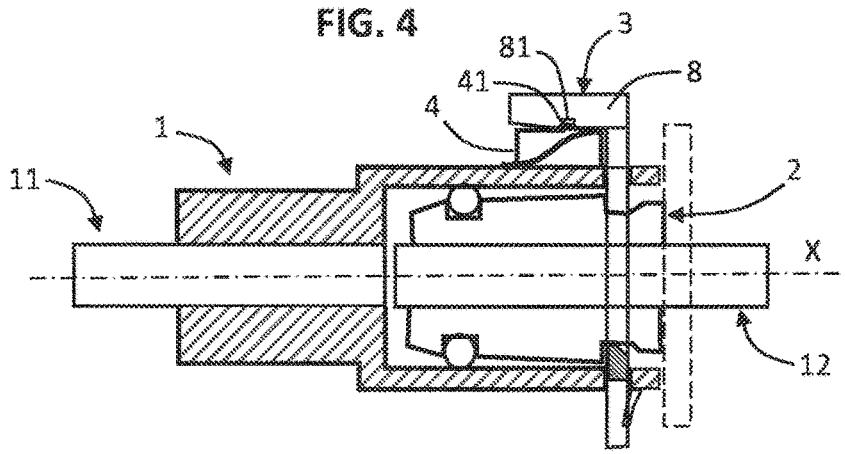
FIGS. 4 and 4A show the connection device of FIG. 2, represented in the coupled and secured state.
Figure 4A:
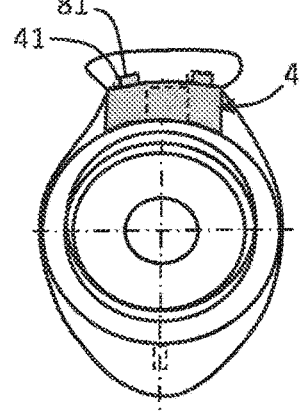

The female plug 1 comprises an internal cylindrical receiving portion 14 of circular cross-section and of a diameter D which is slightly greater than the outside diameter of the male plug intended to be inserted into the female plug. In known manner, an O-ring 6 positioned in a groove of the male plug serves as a sealing means between the male plug and the female plug when they are in the coupling position as represented in FIGS. 3 and 4.

In addition, a movable primary locking device 3 is provided, in the form of a plate 7 arranged transversely to the axis X, with a manipulating portion 8 arranged perpendicular to said plate. In addition, the plate 7 comprises a substantially circular central hole 70 of a slightly larger diameter than the diameter of the male plug; in the example illustrated here, the primary locking device 3 forms a separate part from the female plug 1, allowing the selection of different plastic materials on the basis of various constraints on compatibility with the fluids transported and on elasticity requirements for the deformation of the parts.

The primary locking device 3, also known as the primary lock 3, can be moved between a locked position 30 and an unlocked position 31 which is represented with dotted lines in FIG. 3. The axial hole 70 of the primary lock 3 is of slightly larger diameter than the diameter of the male plug, and in its lower portion there is at least one projection 33 or rim 33 on the hole intended to be received in an annular groove 24 of the male plug.

This projection or rim 33 will also bear against a shoulder 23 formed on the male plug 2, which ensures the retraction-preventing locking function.

When the male plug has been inserted into the complete coupling position (final coupling position) and the primary lock 3 is in its locked position, this prevents the male plug and female plug from leaving the final coupling position, because the shoulder 23 abuts against the projection 33 which is in the upper position.

During the movement of inserting the male plug, its tapered portion 26 pushes the projection 33 downward so that the axial hole 70 of the primary lock 3 is in a substantially coaxial position with the axis X and allows the insertion movement to continue to the final coupling position. During this movement, it is the entire primary lock device which is displaced downward, then returns into the locked position when the male plug and female plug reach the final coupling position.

The primary lock is biased toward the locked position by means of an elastic biasing element 5; in the example illustrated, this is an elastic tongue 5 which may come from the cylindrical body 10 of the female plug or may come from the manipulation portion 8 of the primary lock 3. Alternatively, this biasing may be provided by a conventional spring.

It remains possible to unlock the primary lock: one simply needs to press the manipulation portion 8 of the primary lock 3 (arrow F) to push the primary lock back to the unlocked position, in which case the projection 33 clears the shoulder 23 and the male plug can be removed from the housing of the female plug.

It should be noted that due to the reaction of the O-ring or of a specifically provided biasing force, the male plug may advantageously retract as soon as the primary lock releases it, providing the user with definite feedback that unlocking has occurred; as the final coupling position is therefore unstable, this arrangement also ensures engagement of the primary lock.

In the context of this document, the term 'locked position' for the primary lock 3 denotes the physical position represented in FIGS. 2 and 4, i.e. the term covers both the initial position (FIG. 2) without a male plug 2 being present and the actual locked position with a male plug inserted and retained in the female plug 1 (FIG. 4).

When it is necessary to make the connection permanent, then a secondary lock 4 is placed in an active position, as represented in FIG. 4.

More specifically, the secondary lock 4 in the illustrated example is in the form of a generally U-shaped part open towards the manipulating portion 8, the inner recess of the U-shape being provided to accommodate the elastic biasing element 5. This secondary lock is placed in an active position represented in FIG. 4, in a position where it is interposed between the cylindrical body of the female plug and the manipulating portion 8 of the primary lock 3.

In addition, this secondary lock has one or more shapes, in this example two hook shapes 41 each provided to cooperate with a corresponding snap-fit recess 81.

With this arrangement, once the secondary lock is engaged in its active position, it is very difficult or impossible to remove it; that position is therefore irreversible. The presence of this secondary lock prevents the primary lock from moving out of its locked position to an unlocked position. A permanent, all-time connection is obtained.

A means may further be provided for preventing the primary lock from leaving its housing; for example an elastic blade 73, arranged on the plate 7 so as to be diametrically opposite the manipulating portion, prevents any upward retraction of the primary lock from the locked position 30.

According to this first embodiment, the male plug is particularly simple because it is rotationally symmetrical about the axis and its only deformable element is an O-ring. A flange 29 may optionally be provided to facilitate gripping and pushing it onto its coupling with the female plug.

According to this first embodiment, the female plug receives the primary lock 3 in a sliding manner transversely to the axis; one will note that the primary lock is here part of the female plug, able to move transversely between two positions but trapped on the female plug (it cannot be removed once it has been inserted); the female plug is also arranged to receive the secondary lock 4, which is then interposed in a manner that prevents movement of the primary lock.

It should also be noted that the primary lock is not in contact with the fluid flowing through the connection; the O-ring 6 sits between the inside of the conduits and said primary lock.

It should be noted that the secondary lock 4 can only be properly engaged if the primary lock 3 is in its locked position (otherwise it cannot engage because there is insufficient space); therefore, if the coupling position has not been properly achieved, insertion of the secondary lock is not possible and this provides the user with clear feedback. This arrangement helps to ensure proper connection.

In the case illustrated here, the secondary lock 4 is a separate piece which is provided when the connection is to be made permanent. Advantageously, the secondary lock can be of a different color than the male and female plugs, so that one can clearly see at a distance whether or not the secondary lock is in place.

Figure 5A:
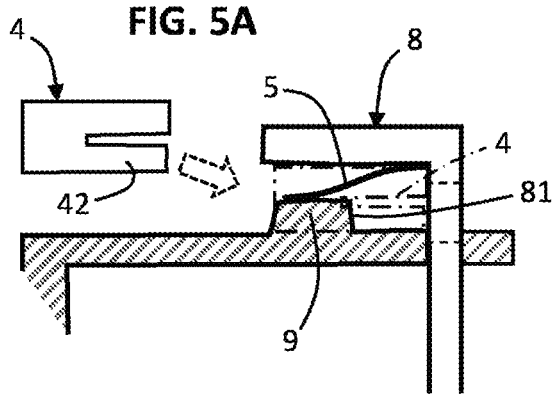
FIGS. 5A-5C show details of a variant of the secondary locking device.
Figure 5B:
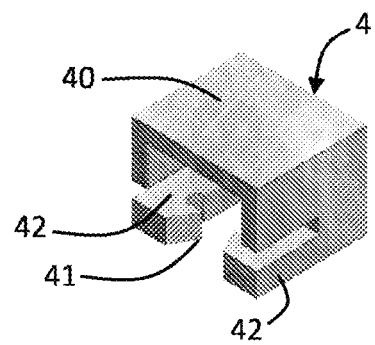
Figure 5C:
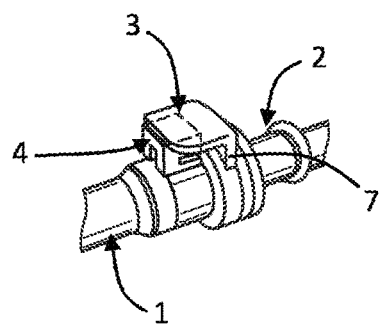

FIGS. 5A-5C show details of an alternative for the secondary locking function. A lug 9 projects from the outer surface of the female plug, this lug being located below the manipulating portion 8. The spring 5 has a base attached to the base of said manipulating portion 8 and a free opposite end which bears against the top of the lug 9. In the example shown, the spring and the lug have substantially the same width in the circumferential direction.

The secondary lock 4 comprises a substantially parallelepipedal body 40 which has two flexible side arms 42 arranged so that they interface with the lug 9. Each of the side arms is provided with a hook shape 41 at its end, configured to move outward during insertion of the secondary lock. Once the hook shapes cross the front wall 81 of the lug, the arms tighten and the lock is clipped in place. In addition, it is impossible for a user to move said arms apart again, and therefore the clipping into place is irreversible. From this state, one can guarantee that the connection cannot be disconnected and therefore the continuity of the chain of sterility can be guaranteed when working under that type of conditions. The chain of sterility can only be broken if the connection is broken or if a special tool is used to remove the secondary lock.

In another variant, not shown, the hooks may be ramped catches allowing the clipping of the secondary lock to be reversible, an aspect which can be advantageous in the case of a secondary lock formed by a specific part separate from the plugs.

FIGS. 6, 7, and 8 illustrate a second embodiment of the fluid connection, comprising a female plug 1 and a male plug 2, as above. In the figures, the female and male plugs are shown in a sectional view cut in a diametrical plane containing the main coupling and locking elements; the major portion of the circumference of the parts thereof is generally symmetrical about the axis X, except at the location of the main locking elements.

Advantageously, the general shape of the male and female plugs can be similar to the products in the SBL series available from the supplier 'Value Plastics', in other words having a generally elliptical cross-section with the largest radial dimension at the clips and a smaller radial dimension elsewhere.

The male plug 2 comprises a right circular cylindrical central portion 13 configured to be received in the female plug and configured to receive a hose or tube 12 forming the second conduit. In addition, the male plug comprises two diametrically opposite resilient clips 3 which form the primary locking device for the connection. The arms 5 carrying the locking clips are elastically deformable in a radial direction; they can flex under stress in the axial direction, but in the absence of external stress they return to a rest position further away from the axis.

The male plug also carries the secondary lock 4 which is in a standby (also called 'inactive') position, as represented in FIGS. 5 and 6, a rear supportive portion 44 being provided for maintaining and guiding said secondary lock in a longitudinal movement. The secondary lock 4 is made of relatively flexible plastic material and is arranged substantially annularly about the rear portion of the male plug.

As for the female plug 1, it comprises recesses 16 extending axially and capable of receiving the abovementioned diametrical clips 3. On the back portion of each recess there is a shoulder 17 which will abut against a projecting shape 37 of the clip. The first fluid conduit 11 is inserted onto the back of the female plug 1.

In FIG. 7, the male and female plugs have reached the final coupling position, in which the projecting shape 37 is locked on the shoulder 17. In this configuration, it is still possible to uncouple the connection by pressing the two diametrical clips 3 towards one another, as indicated by the arrows F. As long as the secondary lock 4 remains in its inactive position, the male and female plugs can be coupled and uncoupled using the primary lock.

When permanent connection is to be established, it is then necessary to move the secondary lock 4 longitudinally from its standby position to its active position as represented in FIG. 8. In this position, it is very difficult if not impossible for fingers to access the areas 38 for pressing the clips of the primary lock, which prevents unintentional disconnection of the fluid connection and ensures that the chain of sterility is maintained.

In addition, the secondary lock is equipped with harpoon shapes 41 which lodge in an external groove 18 of the female plug, making it impossible to withdraw from the active position to the inactive position. This results in a permanently locked connection.

Note that in this second embodiment, the secondary lock 4 could be in its active position from the very beginning, in which case a non-removable connection is obtained at the time of the first coupling.

FIGS. 9, 10, and 11 illustrate a third embodiment of the fluid connection, comprising a female plug 1 and a male plug 2, as above.

As in the second embodiment, the primary locking device is in the form of two diametrically opposite clips arranged on the male plug. The operation of the primary locking device is quite similar to what was described for the second embodiment. However, the secondary lock 4 is arranged on the female plug 1, and has a rear annular portion 46 which surrounds a rear tubular area of the female plug; it also has at least two tabs 47 which extend axially, said tabs being adapted to come respectively between the inner forward portion 39 of each clip 3 and the outer cylindrical body 19 of the female plug, making it impossible for the clips to move from their locked position. The free space necessary for the unlocking movements is then occupied by the tabs 47, preventing any unlocking movement of the clips 3.

In addition, the rear tubular portion of the female plug comprises shapes 15 (here harpoon shapes) which can engage with the secondary lock to retain it in the active position once it has been placed there, as shown in FIG. 11. Once the secondary lock 4 has been moved sufficiently toward the female plug, it has passed beyond the shapes 15 which then act to block any movement of the secondary lock toward the right.

In this configuration, it should be noted that the radial footprint can be decreased, but the axial footprint is slightly greater; conversely, in the second embodiment the axial dimension of the secure connection is optimized, but the radial dimension is slightly greater.

Figure 12:
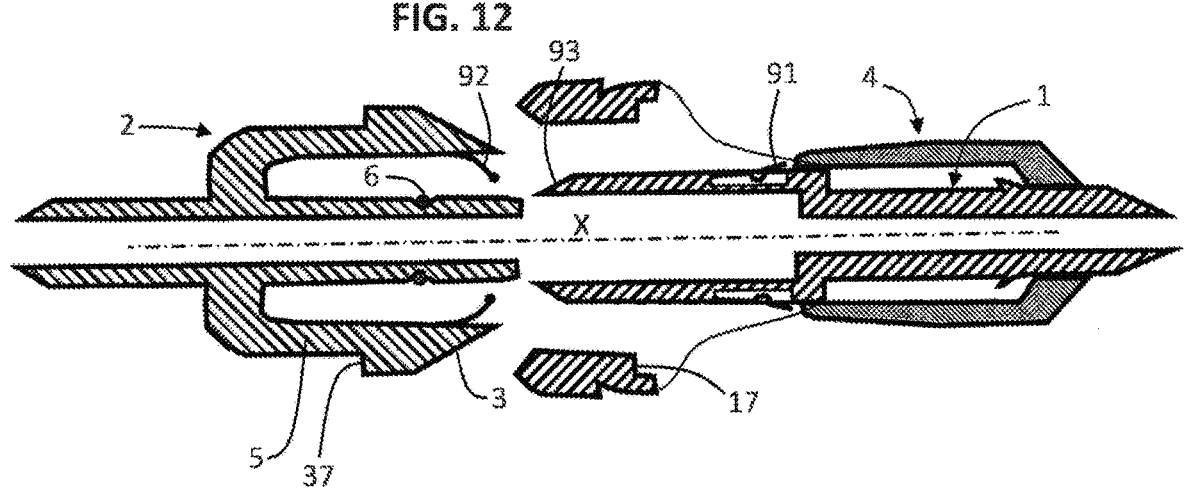
FIGS. 12 and 13 show a variant of the third embodiment.
Figure 13:
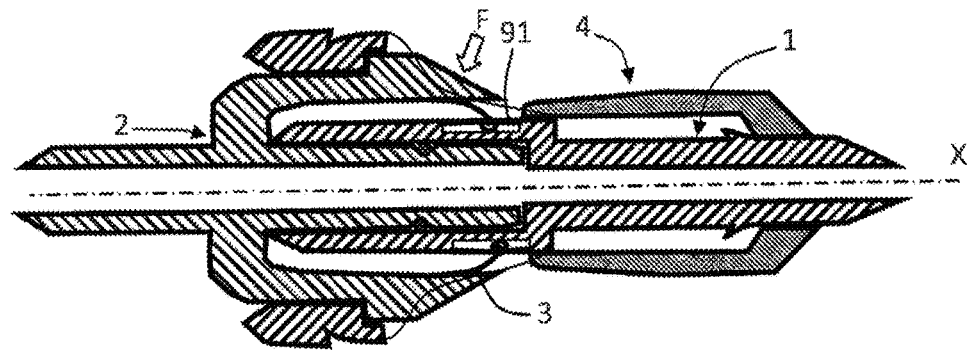

As represented in FIGS. 12 and 13, a variant is provided where the purpose is to prevent the secondary lock 4 from entering its active position as long as the connection is not in the final coupling position and as long as the primary lock is not in its locked position.

More specifically, deformable blades 91 are arranged on the female plug 1, which in their rest position prevent movement of the secondary lock toward its active position (see FIG. 12). Each of these deformable blades 91 is intended to be moved by an elastic catch 92 facing it on the head portion of the clip 3.

As the male plug is inserted into the female plug, the elastic catch 92 first contacts the chamfer 93 of the front edge of the female plug and then comes to press the deformable blade 91 radially inward; this moves the blade inward and out of the way, which allows the secondary lock 4 to move to the left (see FIG. 13).

The secondary lock 4 can thus only leave its inactive position if the final coupling position has been reached and the primary lock is in the locked position.

The other features and functions are identical or similar to what was described above for the third embodiment.

In typical applications of the invention, the diameter of the fluid conduit is typically between 1 and 15 mm. The radial footprint of the plug and socket may be between 10 mm and 30 mm.

Advantageously, the parts described are made of plastic; some of them may be transparent to allow visual monitoring of what is occurring in the fluid conduit; in addition, the secondary lock may be a particularly bright color so that its presence is easily verified (see FIG. 5C).

The invention claimed is:

1. A biopharmaceutical fluid connection device for connecting a first fluid conduit to a second fluid conduit, comprising:
    a female plug, made of plastic and joined to the first fluid conduit;
    a male plug, made of plastic, joined to the second fluid conduit and configured for insertion, parallel to an axial direction, into the female plug and thereby place the male plug and the female plug into a final coupling position;
    a primary locking device, having a locked position in which the primary locking device prevents the male and female plugs from being released from the final coupling position, the primary locking device being a part of the female plug and movable transversely between two positions, the movable primary locking device including a plate arranged transversely to the axial direction; and
    a movable secondary lock, having an active position adapted to prevent the primary locking device from being moved from the locked position,
    wherein the secondary lock is configured to be irreversibly clipped into place in the active position, whereby the fluid connection device can establish a permanent connection of the first and second conduits,
    wherein the secondary lock is a separate part from the female plug and the male plug, so that the locked position is obtained in absence of the secondary lock by assembling the female plug and the male plug together with the primary locking device trapped in the female plug, and
    wherein the primary locking device is arranged on the female plug and is movable in a sliding manner perpendicularly to the axial direction.

2. The device according to claim 1, wherein the secondary locking device prevents operative access to the primary locking device.

3. The device according to claim 2, wherein the primary locking device includes a manipulating portion arranged perpendicular to the plate, the plate having a circular central hole through which the male plug passes, the secondary lock configured to be interposed between a cylindrical body of the female plug and the manipulating portion to achieve the active position.

4. The device according to claim 1, wherein the secondary locking device prevents the primary locking device from moving out of the locked position.

5. The device according to claim 1, wherein the secondary lock is configured so as to be clipped into place with the assembled female and male plug upon said primary locking device being placed into the locked position.

6. The device according to claim 1, wherein the primary locking device is biased toward the locked position by elastic biasing means.

7. The device according to claim 1, wherein the secondary locking device can only be placed in the active position if the primary locking device is in the locked position.

8. The device according to claim 1, wherein the secondary locking device can only be placed in the active position if the male and female plugs are in the final coupling position and if simultaneously the primary locking device is in the locked position.

9. The device according to claim 1, wherein the secondary locking device is configured to be arranged on one of the male or female plugs, and is configured to be moved from an inactive position to the active position in order to lock the connection permanently.

10. The device according to claim 1, wherein the primary locking device is a part distinct from the female plug.

11. The device according to claim 1, wherein the plate of the primary locking device has an opening through which the male plug is received.

12. The device according to claim 1, wherein the secondary lock is configured to cooperate with a snap-fit recess provided in a manipulating portion of the primary locking device.

13. A biopharmaceutical fluid connection device for connecting a first fluid conduit to a second fluid conduit, comprising:
- a female plug, made of plastic and joined to the first fluid conduit;
- a male plug, made of plastic, joined to the second fluid conduit and configured for insertion, parallel to an axial direction, into the female plug and thereby place the male plug and the female plug into a final coupling position;
- a primary locking device, having a locked position in which the primary locking device prevents the male and female plugs from being released from the final coupling position, the primary locking device being a part of the female plug and movable transversely between two positions, the movable primary locking device including a plate arranged transversely to the axial direction; and
- a movable secondary lock, having an active position adapted to prevent the primary locking device from being moved from the locked position, wherein the secondary lock is configured to be irreversibly clipped into place in the active position, whereby the fluid connection device can establish a permanent connection of the first and second conduits, wherein the secondary lock is a separate part from the female plug and the male plug, so that the locked position is obtained in absence of the secondary lock by assembling the female plug and the male plug together with the primary locking device trapped in the female plug, and wherein the female plug includes a housing that extends transversally to the axial direction for receiving the primary locking device in the locked position, the secondary lock extending outside the housing to cooperate with a manipulating portion of the primary locking device which extends outside the housing in the locked position.

* * * * *